United States Patent [19]

Kondo et al.

[11] Patent Number: 4,910,352

[45] Date of Patent: Mar. 20, 1990

[54] METHOD OF PREPARING 1,1,1-TRIFLUORO-2,2-DICHLOROETHANE FROM TRIFLUOROTRICHLOROETHANE

[75] Inventors: Takeshi Kondo, Sayama; Satoshi Yoshikawa, Saitama, both of Japan

[73] Assignee: Central Glass Company Limited, Ube, Japan

[21] Appl. No.: 255,600

[22] Filed: Oct. 11, 1988

[30] Foreign Application Priority Data

Oct. 12, 1987 [JP] Japan .................. 62-257001

[51] Int. Cl.$^4$ .................. C07C 17/24; C07C 17/38; C07C 19/02
[52] U.S. Cl. .................. 570/176; 570/180
[58] Field of Search .................. 570/176

[56] References Cited

U.S. PATENT DOCUMENTS 4,145,368 3/1979 Sweeney et al. .................. 260/653

FOREIGN PATENT DOCUMENTS

| 40475 | 8/1965 | German Democratic Rep. .................. 570/176 |
| 58-222038 | 12/1983 | Japan . |
| 53600 | 7/1967 | Poland .................. 570/176 |
| 939920 | 10/1963 | United Kingdom .................. 570/176 |

OTHER PUBLICATIONS

Madai et al., "Chem. Abstracts", vol. 58 (1963) 11200h.
"Chemistry in Hydrogen Fluoride V. Catalysts for Reaction of Halogenated Olefins", by A. E. Feiring, Journal of Fluorine Chemistry, 13 (1979), pp. 7–18.

Primary Examiner—J. E. Evans
Attorney, Agent, or Firm—Fleit, Jacobson, Cohn, Price, Holman & Stern

[57] ABSTRACT $CF_3CHCl_2$ is easily obtained at good yield by reduction of $CF_3CCl_3$ in an aqueous solution of $Na_2SO_3$ and an acid acceptor such as hydroxide, carbonate or acetate of an alkali metal or alkaline earth metal. Usually the reduction reaction is carried out at 60°–150° C. under gauge pressure of 0–10 kg/cm$^2$. The aimed compound can easily be recovered by separating the reaction liquid into organic and aqueous layers, and the waste aqueous solution contains no compound difficult to dispose of.

4 Claims, No Drawings

METHOD OF PREPARING 1,1,1-TRIFLUORO-2,2-DICHLOROETHANE FROM TRIFLUOROTRICHLOROETHANE

BACKGROUND OF THE INVENTION

This invention relates to a method of preparing 1,1,1-trifluoro-2,2-dichloroethane $CF_3CHCl_2$ from 1,1,1-trifluoro-2,2,2-trichloroethane.

1,1,1-Trifluoro-2,2-dichloroethane (will be referred to as fluorocarbon 123) can be fluorinated into $CF_3CHClF$ (fluorocarbon 124) which is useful as a working fluid or can be oxidized and hydrolyzed into trifluoroacetic acid. Furthermore, fluorocarbon 123 is expected to serve as a substitute for fluorocarbon 11 which is used as a foaming agent for polyurethane resins.

According to J. Fluorine Chem., 13, 7–18 (1979), $CF_3CHCl_2$ is obtained by fluorinating tetrachloroethylene with hydrogen fluoride in the presence of a metal halide catalyst, but by this method the yield of $CF_3CHCl_2$ is very low.

Also it is known that $CF_3CHCl_2$ can be derived from 1,1,1-trifluoro-2,2,2-trichloroethane. USP 4,145,368 shows preparing $CF_3CHCl_2$ by subjecting $CF_3CCl_3$ (fluorocarbon 113a) and $CF_3CH_2Cl$ (fluorocarbon 133a) to a disproportionation reaction on a chromium oxide catalyst, but the reported yield of $CF_3CHCl_2$ is only about 14%. JP-A 58-222038 shows that $CF_3CHCl_2$ is obtained at good yield by reduction of $CF_3CCl_3$ with zinc dust in a protic solvent. However, this method is inconvenient for industrial adoption because the disposal of by-produced zinc chloride and unreacted zinc dust is not easy and also because distillation is necessary for separating $CF_3CHCl_2$ from the protic solvent.

SUMMARY OF THE INVENTION

It is an object of the present invention to provide an industrially adoptable and favorable method for preparing $CF_3CHCL_2$ efficiently and economically.

According to the invention there is provided a method of preparing $CF_3CHCl_2$, comprising subjecting $CF_3CCl_3$ to a reduction reaction in an aqueous solution of sodium sulfite and an acid acceptor.

In the reaction according to the invention one chlorine atom of the starting compound is easily substituted by hydrogen atom originated from the aqueous solution containing sodium sulfite. This reduction reaction is accompanied by formation of hydrogen chloride, but this acidic by-product readily neutralizes by reacting with the acid acceptor contained in the aqueous solution. For example, the acid acceptor is an alkali metal or alkaline earth metal hydroxide or carbonate.

It is suitable to carry out the reaction according to the invention at a temperature of from about 60° C. to about 150° C. preferably under moderate pressure.

The starting compound employed in this invention, $CF_3CCl_3$, can easily be prepared at good yield by isomerizing $CCl_2FCClF_2$, which is an industrially available material, using an aluminum halide catalyst.

The method of the invention gives $CF_3CHCl_2$ at good yield, and this product can easily be separated from the aqueous solution. The waste aqueous solution contains only harmless salts such as sodium sulfate and an alkali metal or alkaline earth metal chloride and, hence, can very easily be disposed of. This is an important merit of the method according to the invention.

DESCRIPTION OF THE PREFERRED EMBODIMENTS

The reduction reaction according to the invention is usually carried out in a reactor of autoclave type. The reactor is charged with predetermined quantities of water, $CF_3CCl_3$, sodium sulfite and a selected acid acceptor, and these materials are mixed together. The reaction is accomplished by keeping the mixture in the reactor heated at a predetermined temperature while continuing stirring. The heating is terminated when it is found that at the employed reaction temperature the pressure in the reactor is no longer rising. After cooling the reaction liquid is allowed to separate into organic and aqueous layers, and the organic layer is recovered to obtain the aimed compound. Isolation and purification of obtained $CF_3CHCl_2$ can be accomplished by usual operations including distillation.

Sodium sulfite for use in this method may be either anhydrous or containing water of crystallization. It is suitable to use 1 to 2 mols, preferably 1.2 to 1.5 mol, of $Na_2SO_3$ per 1 mol of $CF_3CCl_3$. If the amount of sodium sulfite is less than 1 mol the intended reduction reaction does not well proceed. Use of more than 2 mols of sodium sulfite is uneconomical because practically the same result is obtained whether the amount of this reagent is just 2 mols or more than 2 mols.

As an acid acceptor indispensable for this method it is convenient to use hydroxide, carbonate or acetate of either an alkali metal or an alkaline earth metal, though it is also possible to make a selection from other compounds that are soluble in water and serve as acid acceptor. For example, it is suitable and convenient to use sodium hydroxide, potassium hydroxide, calcium hydroxide, sodium carbonate, sodium hydrogen carbonate, potassium carbonate or sodium acetate. In general the minimum quantity of the compound used as acid acceptor is 1 mol per 1 mol of $CF_3CCl_3$ subjected to the reaction. If the amount of the acid acceptor is less than 1 mol the conversion of $CF_3CCl_3$ remains relatively low. it is preferable to use 1.1 to 1.5 mol of an acid acceptor compound per 1 mol of $CF_3CCl_3$.

The quantity of water for dissolving sodium sulfite and the acid acceptor is not specified. It is necessary that the entire quantities of sodium sulfite and the acid acceptor are dissolved in water at the employed reaction temperature, but it is unnecessary to use a large excess of water. The aqueous solution for the reaction according to the invention may be either neutral or basic.

Usually the reaction according to the invention is carried out at a temperature ranging from about 60° C. to about 150° C. At temperatures below 60° C. the reaction does not smoothly proceed, and it takes a very long time to complete the reaction. When the reaction is carried out at a temperature above 150° C. selectively low. The preferred range of the reaction temperature is from about 90° C. to about 110° C. Although it is possible to carry out this reaction under normal pressure, usually it is favorable to carry out the reaction under a gauge pressure of up to about 10 kg/cm$^2$, and preferably in the range from 6 to 8 kg/cm$^2$.

The invention is illustrated by the following nonlimitative examples.

EXAMPLE 1

A stainless steel autoclave having a capacity of 1 liter was charged with 93.8 g (0.5 mol) of $CF_3CCl_3$, 94.5 g (0.75 mol) of anhydrous sodium sulfite, 20 g (0.5 mol) of sodium hydroxide and 750 ml of water. With continuous stirring the mixture in the autoclave was kept heated at 95–105° C. for 5 hr under pressure of 7–8 kg/cm$^2$ (gauge pressure). After that the autoclave was cooled in iced water.

The cooled reaction liquid was taken out of the autoclave and, under normal pressure, was allowed to separate into an aqueous layer and an organic layer. As the result 66.7 g of organic matter was recovered. Gas chromatography analysis of the recovered organic matter revealed that the conversion of the starting fluorocarbon $CF_3CCl_3$ had reached 92.8% and that in the reaction the selectivity to the aimed fluorocarbon $CF_3CHCl_2$ was 84.1%. The reaction product included $CF_2=CCl_2$ (3.5%), $CF_2=CHCl$ (1.2%) and $CF_3CH_2Cl$ (0.5%) and, besides, some low boiling points gases of which the identification was omitted.

EXAMPLES 2–6

In these examples the process of Example 1 was repeated except that the acid acceptor was changed and that the reaction was carried out under different pressures. The particulars of the changes were as shown in the following table. The results are also shown in the table.

In the table the parenthesized figures represent the fluorocarbons found in the reaction product, as noted below the table. Besides these fluorocarbons some low boiling points gases were formed in every example.

| Acid Acceptor | Pressure (gauge) (kg/cm$^2$) | Conversion of $CF_3CCl_3$ (%) | Selectivity (%) | | | |
|---|---|---|---|---|---|---|
| | | | (1) | (2) | (3) | (4) |
| Ex. 2 NaOH 30.0 g | 7 | 94.8 | 60.5 | 18.7 | 6.2 | 1.8 |
| Ex. 3 Na$_2$CO$_3$ 40.0 g | 6 | 64.9 | 75.7 | 8.3 | 4.1 | 1.7 |
| Ex. 4 NaHCO$_3$ 63.0 g | 14 | 83.5 | 64.4 | 15.5 | 6.7 | 2.2 |
| Ex. 5 CH$_3$COONa 61.5 g | 8 | 93.5 | 88.2 | 1.2 | 0.4 | 0.2 |
| Ex. 6 Ca(OH)$_2$ 28.1 g | 8 | 93.2 | 56.6 | 15.8 | 6.0 | 2.4 |

In every example, 93.8 g of $CF_3CCl_3$ and 94.5 g of $Na_2SO_3$ were used.

(1): $CF_3CHCl_2$
(2): $CF_2=CCl_2$
(3): $CF_2=CHCl$
(4): $CF_3CH_2Cl$

What is claimed is:

1. A method of preparing 1,1,1-trifluoro-2,2-dichloroethane, comprising subjecting 1,1,1-trifluoro-2,2,2-trichloroethane to a reduction reaction in an aqueous solution of sodium sulfite and an acid acceptor selected from the group consisting of alkali metal hydroxides, carbonates and acetates and alkaline earth metal hydroxides, carbonates and acetates; wherein the molar ratio of said sodium sulfite to said 1,1,1-trifluoro-2,2,2-trichloroethane is from 1:1 to 2:1 and wherein the reaction is carried out at a temperature in the range from 90 to 110° C.

2. A method according to claim 1, wherein the molar ratio of said acid acceptor to said 1,1,1-trifluoro-2,2,2-trichloroethane is in the range from 1:1 to 1.5:1.

3. A method according to claim 1, wherein said reaction is carried out under gauge pressure of from 0 to 10 kg/cm$^2$.

4. A method according to claim 1, wherein said acid acceptor is selected from the group consisting of sodium hydroxide, potassium hydroxide, calcium hydroxide, sodium carbonate, sodium hydrogen carbonate and sodium acetate.

* * * * *